US006999558B2

(12) United States Patent
Okoda

(10) Patent No.: US 6,999,558 B2
(45) Date of Patent: Feb. 14, 2006

(54) MOBILE RADIOGRAPHIC APPARATUS, RADIOGRAPHIC SYSTEM, RADIOGRAPHIC METHOD, PROGRAM, COMPUTER-READABLE STORAGE MEDIUM, AND INFORMATION SYSTEM

(75) Inventor: Keiji Okoda, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 98 days.

(21) Appl. No.: 10/436,868

(22) Filed: May 13, 2003

(65) Prior Publication Data

US 2003/0219100 A1 Nov. 27, 2003

(30) Foreign Application Priority Data

May 21, 2002 (JP) ............................. 2002-146218
May 21, 2002 (JP) ............................. 2002-146345
Apr. 3, 2003 (JP) ............................. 2003-100637

(51) Int. Cl.
*H01G 1/26* (2006.01)
(52) U.S. Cl. ........................... 378/102; 378/115; 705/7
(58) Field of Classification Search ................ 378/4, 378/114–115, 901, 116, 207, 102, 198, 68–69; 709/227, 200; 705/3, 2, 6–7; 707/7; 700/13
See application file for complete search history.

(56) References Cited

U.S. PATENT DOCUMENTS

| | | | | |
|---|---|---|---|---|
| RE36,415 E | * | 11/1999 | McKenna | 378/4 |
| 6,084,939 A | * | 7/2000 | Tamura | 378/98.2 |
| 6,287,257 B1 | | 9/2001 | Matichuk | |
| 6,412,980 B1 | * | 7/2002 | Lounsberry et al. | 378/207 |
| 6,481,887 B1 | | 11/2002 | Mirabella | |
| 6,491,430 B1 | * | 12/2002 | Seissler | 378/207 |
| 6,501,827 B1 | * | 12/2002 | Takasawa | 378/116 |
| 6,504,897 B1 | * | 1/2003 | Yonekawa | 378/63 |
| 6,504,987 B1 | * | 1/2003 | Macken et al. | 385/135 |
| 6,574,518 B1 | * | 6/2003 | Lounsberry et al. | 700/90 |
| 6,614,873 B1 | * | 9/2003 | Taylor et al. | 378/62 |
| 6,694,367 B1 | * | 2/2004 | Miesbauer et al. | 709/227 |
| 6,806,487 B1 | * | 10/2004 | Tamakoshi et al. | 250/586 |
| 2002/0087359 A1 | * | 7/2002 | Bocionek | 705/2 |
| 2004/0028174 A1 | * | 2/2004 | Koren | 378/4 |
| 2004/0138923 A1 | * | 7/2004 | Routh et al. | 705/2 |
| 2005/0080326 A1 | * | 4/2005 | Mathew | 600/407 |

FOREIGN PATENT DOCUMENTS

DE 199 41 237 A1 8/1999
DE 101 17 044 A1 4/2001

(Continued)

OTHER PUBLICATIONS

Wong, T.C. Stephan "A Hospital Integrated Framework Multimodality Image Base Management" IEEE Transactions on Systems, Man, And Cybernectics-Part A: System and Human vol. 26 No. 4 Jul. 1996.

(Continued)

*Primary Examiner*—David V. Bruce
*Assistant Examiner*—Hoon Song
(74) *Attorney, Agent, or Firm*—Morgan & Finnegan, LLP

(57) ABSTRACT

In a radiographic method using a mobile radiographic apparatus including an image generating unit which includes photoelectric conversion elements and generates radiographic image data of an object, key information for selecting radiographic request information is transmitted to an external information system having the radiographic request information. The radiographic request information transmitted from the information system is received. The operation of the image generating unit is controlled based on the received radiographic request information.

11 Claims, 12 Drawing Sheets

FOREIGN PATENT DOCUMENTS

| | | |
|---|---|---|
| EP | 1 336 378 A1 | 8/2000 |
| JP | 55-12429 | 1/1980 |
| JP | 56-11395 | 2/1981 |
| JP | 2001-299743 | 10/2001 |
| JP | 2002-125960 | 5/2002 |
| WO | WO02/36014 A1 | 5/2002 |

OTHER PUBLICATIONS

European Search Report, dated Sep. 1, 2003.
Chinese Office Action with English Translation dated Oct. 1, 2004.

* cited by examiner

MOBILE RADIOGRAPHIC APPARATUS, RADIOGRAPHIC SYSTEM, RADIOGRAPHIC METHOD, PROGRAM, COMPUTER-READABLE STORAGE MEDIUM, AND INFORMATION SYSTEM

FIELD OF THE INVENTION

The present invention relates to radiography using a mobile radiographic apparatus.

BACKGROUND OF THE INVENTION

Conventionally, as the commonest imaging method for X-ray imaging, the film/screen method has been used. In this method, imaging is performed by using a combination of a light-sensitive film and a phosphor having sensitivity to X-rays. Phosphors made of a rare-earth material that emits light upon being irradiated with X-rays are held in tight contact with the two surfaces of a light-sensitive film. X-rays transmitted through an object to be imaged are converted into visible light by the phosphors, and the light is captured by the light-sensitive film. The latent image formed on the light-sensitive film is developed by a chemical treatment, thereby visualizing the image.

As the second imaging method, a method called the computed radiography (CR) method has also been put into practice. In this method, a radiation transmission image is temporarily stored as a latent image in a phosphor, and the latent image is read out afterward by irradiating the phosphor with exciting light. When, for example, a certain type of phosphor is irradiated with radiations such as X-rays, αrays, βrays, γrays, electron rays, or ultraviolet rays, part of the energy of the radiations is stored in the phosphor. It is also known that when this phosphor is irradiated with exciting light such as visible light, the phosphor exhibits photostimulated luminescence in accordance with the stored energy.

A phosphor exhibiting such a property is called a storage phosphor or photostimulated phosphor. Radiation image information recording/playback systems have been proposed in, for example, Japanese Patent Laid-Open Nos. 55-12429 and 56-11395. In such a system, by using this storage phosphor, radiation image information of an object such as a human body is temporarily stored in a storage phosphor sheet. Thereafter, this storage phosphor sheet is scanned with exciting light such as laser light to produce photostimulated luminescence light. By photoelectrically reading the obtained photostimulated luminescence light, an image signal is acquired. On the basis of this image signal, a radiographic image of the object is output as a visible image to a recording material such as a photographic light-sensitive material or a display device such as a CRT.

With the recent advances in semiconductor process techniques, an apparatus for taking an X-ray image by using a semiconductor sensor in the same manner has been developed as the third imaging method. A system of this type is advantageous over a conventional radiographic system in that it can record images in a very wide radiation exposure range. More specifically, X-rays in a wide dynamic range are read by a photoelectric conversion means to be converted into an electrical signal. By using this electrical signal, a radiographic image is output as a visible image to a recording material such as a photographic light-sensitive material or a display device such as a CRT. This makes it possible to obtain a radiographic image that is robust against variations in the amount of exposure to radiation.

FIG. 6 is a schematic view of a radiation imaging system using the above semiconductor sensor. An X-ray imaging apparatus 1 incorporates an X-ray detection sensor 2 having a detection surface constituted by a plurality of two-dimensionally photoelectric conversion elements. An object to be imaged is irradiated with the X-rays emitted from an X-ray generating unit 3 of the X-ray imaging apparatus 1. The X-rays transmitted through the object S are detected by the X-ray detection sensor 2. The image signal output from the X-ray detection sensor 2 is subjected to digital image processing in an image processing unit 4. The resultant data is then displayed as an X-ray image of the object S on a monitor 5.

With recent improvements in information networks in hospitals, information systems called a hospital information system (HIS), a radiology information system (RIS), a picture archiving and communication system (PACS), and the like have been developed as systems which handle information on networks. These systems are closely related to the operation of X-ray imaging apparatuses.

The hospital information system handles overall in-hospital management information such as patient information (e.g., patient IDs, patient names, sexes, and dates of birth) and accounting information. The radiology information system manages information concerning imaging operation, e.g., receiving an imaging request from a diagnosis/treatment department and outputting an imaging request to the radiology department upon clarifying a specific patient, specific region, and specific imaging equipment to be used for imaging operation. The picture archiving and communication system performs archiving management of image data, e.g., archiving sensed image data and retrieving and distributing images upon reception of visual check requests for past images.

X-ray imaging apparatuses in a hospital include a stationary apparatus that is fixed in an imaging room and a mobile apparatus which can move in the hospital. The mobile apparatus can be carried to a patient's room, operating room, intensive care unit, accident ward, or the like to perform X-ray imaging for a patient who cannot come to the imaging room. Obviously, the stationary X-ray imaging apparatus is connected online to each information system in the hospital. However, the mobile X-ray imaging apparatus is not connected to any information system in the hospital.

FIG. 7 shows the schematic arrangement of a conventional information system in a hospital.

An information system 11 is connected to a radiology information system 12 and exchanges information concerning patient information, imaging, and the like. Upon reception of an X-ray imaging request, the radiology information system 12 generates X-ray imaging request documents with necessary information being completed, and outputs them, as documents 16. In a large-scale hospital, a plurality of mobile X-ray imaging apparatuses 13, 14, and 15 are prepared in each diagnosis/treatment department or ward, and a plurality of X-ray imaging technicians simultaneously perform imaging.

In order to make the mobile X-ray imaging apparatuses 13, 14, and 15 respectively perform requested X-ray imaging operations, an operator who determines tasks sorts the documents 16 (to documents 17, 18, and 19) according to the X-ray imaging. apparatuses to be used, and assigns the respective mobile X-ray imaging apparatuses to the X-ray imaging technicians in charge. Upon reception of the request, each X-ray imaging technician moves together with a mobile X-ray imaging apparatus in a corresponding shared range to perform imaging. After the imaging, the technician inputs the imaging result to the radiology information system 12 through a request document.

Upon reception of requests, each X-ray imaging technician rearranges first the distributed request documents in imaging order. In this case, the imaging technician rearranges the request documents based on the patients' room numbers written on the documents in consideration of the arrangement of the rooms and the most efficient imaging route. Each imaging technician then moves together with a mobile X-ray imaging apparatus in a corresponding shared range and performs imaging in accordance with the order.

The imaging apparatus designed to acquire external information concerning imaging operation through a portable storage medium or communication means is known in Japanese Patent Laid-Open No. 2002-125960, which is a portable imaging apparatus designed to acquire sensed images by using an imaging means including photoelectric conversion elements.

As described above, conventional mobile X-ray imaging apparatuses are not connected to the network in a hospital. According to the film/screen method, since no image is digitalized, both the stationary and mobile X-ray imaging apparatuses are not generally connected to the network in a hospital. In the computed radiography method, a reading device for photostimulated phosphors is of a stationary type and is generally connected to the network in a hospital.

In using a mobile X-ray imaging apparatus, photostimulated phosphors are stored in cases called cassettes one by one and carried to be used for imaging as in the case of ordinary films, and each cassette having undergone imaging operation is carried to a reading device to be read. The mobile X-ray imaging apparatus is not therefore connected to the network in a hospital.

With a recent improvement in the performance of mobile X-ray imaging apparatuses and for the purpose of reducing the burdens on patients to be imaged, an increasing number of imaging operations are performed by using mobile X-ray imaging apparatuses. The conventional operation based on documents has posed problems in terms of poor input/output efficiency and poor reliability related to errors in writing, posting errors, and the like. In addition, since each technician determined an imaging order, he/she did not always follow the most efficient, shortest route, resulting in poor imaging efficiency.

In the third method, when an X-ray detection sensor is to be used, a stationary X-ray imaging apparatus is generally connected to the network in a hospital. When an X-ray detection sensor is to be used for a mobile X-ray imaging apparatus, since a control device and image storage device for the X-ray detection sensor are incorporated in the mobile X-ray imaging apparatus, the operation efficiency becomes very poor unless the apparatus has some means for connecting to the network in the hospital.

For example, at times it becomes necessary to manually input patient information or temporarily store image information in a portable medium and send the information to an information system through the medium. The operation time may undesirably become long or a data entry error may occur. In addition, since there has been no system for determining an imaging order, the imaging efficiency has been poor. According to the mobile (portable) imaging apparatus disclosed in Japanese Patent Laid-Open No. 2002-125960 described above, there is no need to manually input patient information, and imaging information can be efficiently acquired. If, however, operation and the like using a plurality of mobile imaging apparatuses are assumed, it is necessary to select imaging information for each mobile imaging apparatus in externally acquiring imaging information.

SUMMARY OF THE INVENTION

The present invention has been made to solve the above problems, and has an object to realize an efficient, effective work flow associated with radiography using mobile a radiographic apparatus.

According to the present invention, the foregoing object is attained by providing a mobile radiographic apparatus comprising:

an image generating unit, including a photoelectric conversion element, arranged to generate radiographic image data of an object;

a transmission unit arranged to transmit, to an external information system having radiographic request information, key information for selecting the radiographic request information;

a reception unit arranged to receive the radiographic request information transmitted from the information system; and a control unit arranged to control operation of the image generating unit based on the radiographic request information received by the reception unit.

Other features and advantages of the present invention will be apparent from the following description taken in conjunction with the accompanying drawings, in which like reference characters designate the same or similar parts throughout the figures thereof.

DETAILED DESCRIPTION OF THE PREFERRED EMBODIMENTS

The preferred embodiments will be exemplary described in detail below with reference to the accompanying drawings. Note that the constituent elements described in these embodiments are merely examples, and the range of the present invention is not limited to them.

<First Embodiment>

Figure 1:
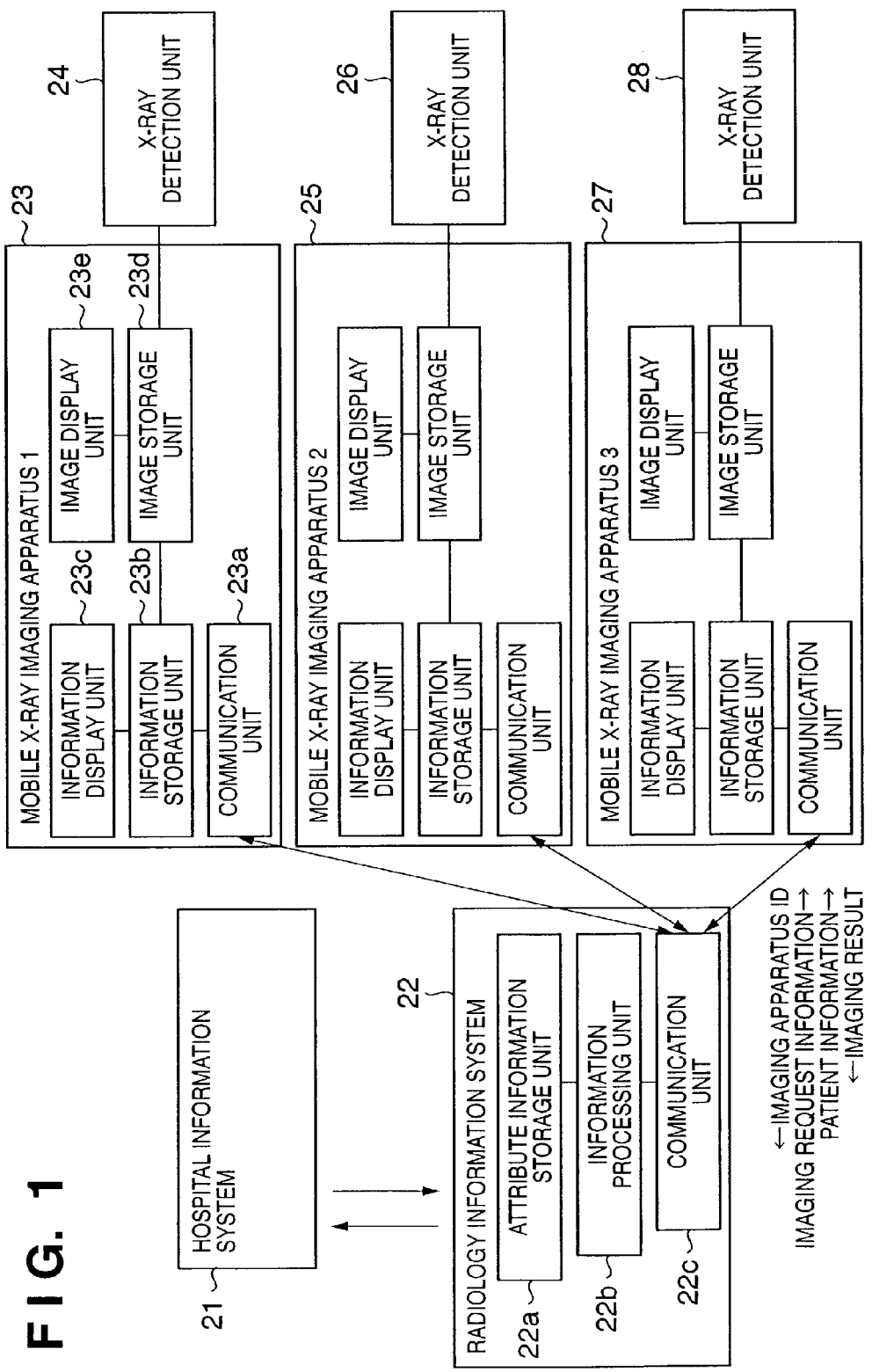
FIG. 1 is a block diagram showing the schematic arrangement of an X-ray imaging system according to the first embodiment of the present invention.

FIG. 1 is a block diagram showing the schematic arrangement of an X-ray imaging system according to the first embodiment of the present invention.

Referring to FIG. 1, reference numeral 21 denotes a hospital information system; 22, a radiology information system; 23, 25, and 27, first, second, and third mobile X-ray imaging apparatuses; and 24, 26, and 28, X-ray detection units respectively included in the mobile X-ray imaging apparatuses 23, 25, and 27. The mobile X-ray imaging apparatuses 23, 25, and 27 have the same arrangement. The following description will be made by using the mobile X-ray imaging apparatus 23 as a typical example.

As described above, the hospital information system 21 handles overall in-hospital management information such as patient information (e.g., patient IDs, patient names, sexes, and dates of birth) and accounting information. Likewise, the radiology information system 22 manages imaging request information concerning imaging operation, e.g., receiving an imaging request from the diagnosis/treatment department and outputting an imaging request to the radiology department upon clarifying a specific patient, specific region, and specific imaging equipment to be used for imaging operation. The hospital information system 21 and radiology information system 22 are connected to each other through a network inside the hospital to exchange necessary information with each other.

The radiology information system 22 in the first embodiment has an attribute information storage unit 22a which stores the attribute information of each mobile X-ray imaging apparatus. The "attribute information" in this case is information concerning a specific range of patients inside the hospital for which each mobile X-ray imaging apparatus is to perform imaging operation. This information includes, for example, a standby place for each apparatus, the name of a target diagnosis/treatment department, and the name of a technician in charge. These pieces of attribute information are stored in association with the imaging apparatus IDs (identification information) of the respective mobile X-ray imaging apparatuses.

Note that attribute information is used to select (retrieve) imaging request information stored in an imaging request information storage unit (not shown) in the radiology information system 22, and hence is associated with the imaging request information. That is, an imaging apparatus ID and attribute information each function as selection (retrieval) key information indirectly or directly associated with imaging request information. This imaging request information storage unit may be realized by, for example, an external storage device such as a hard disk, or a memory such as a RAM or EEPROM.

An information processing unit 22b in the radiology information system 22 has a function of distributing (assigning) pieces of imaging request information to the respective mobile X-ray imaging apparatuses by using attribute information from the attribute information storage unit 22a, when it is necessary to give imaging requests to the mobile X-ray imaging apparatuses. The pieces of imaging request information distributed to the respective mobile X-ray imaging apparatuses are wirelessly transmitted to the mobile X-ray imaging apparatuses 23, 25, and 27 by a communication unit 22c.

In the mobile X-ray imaging apparatus 23, a communication unit 23a has a storage medium storing the imaging apparatus ID of each mobile X-ray imaging apparatus, and transmits first the imaging apparatus ID from the mobile X-ray imaging apparatus 23 to the radiology information system 22.

In the radiology information system 22, the information processing unit 22b recognizes the imaging apparatus ID, and transmits the imaging request information sorted according to the attribute information to the corresponding mobile X-ray imaging apparatus. The patient information sent from the hospital information system 21 is also attached to the imaging request information. The mobile X-ray imaging apparatus 23 has an information storage unit 23b which stores the imaging request information and patient information input by communication and an information display unit 23c which displays these pieces of information.

For example, the mobile X-ray imaging apparatus 23 transmits the imaging apparatus ID of a processing target by operating a switch (not shown) by the operator (X-ray imaging technician), and acquires imaging request information and patient information. The operator can then see the imaging request information, patient information, and the like on the information display unit 23c. The operator performs imaging operation in accordance with these pieces of information.

Each of the X-ray detection units (to be also referred to as radiographic detection units) 24, 26, and 28 incorporates an X-ray detection sensor (not shown) having a detection surface constituted by a plurality of photoelectric conversion elements arranged two-dimensionally (in one plane). The photoelectric conversion elements convert X-ray photons to electrons directly or convert light photons, to which a scintillator converts X-ray photons, to electrons. An object is irradiated with X-rays emitted from the X-ray generating unit (not shown) of the mobile X-ray imaging apparatus, and X-rays transmitted through the object are detected by the X-ray detection sensor.

The image signal output from the X-ray detection sensor is subjected to digital image processing in an image processing unit (not shown). The resultant data is stored in an image storage unit 23d in the mobile X-ray imaging apparatus 23 and displayed as an X-ray image of the object on an image display unit 23e. After the imaging operation, imaging result information (sensed image data, imaging conditions, and the like) concerning the imaging operation which is required to be returned to the radiology information system 22 is sent to the radiology information system 22 through the communication units 23a and 22c and managed as an imaging result.

The sensed image data acquired by the radiology information system 22 is stored in a picture archiving and communication system by using an offline medium (not shown) and can be displayed in accordance with a request.

Note that the hospital information system 21, radiology information system 22, and mobile X-ray imaging apparatuses 23, 25, and 27 each include standard constituent elements (e.g., a CPU, RAM, ROM, hard disk (external storage device), network interface, display, keyboard, and mouse) mounted in a general-purpose computer.

Figure 2:
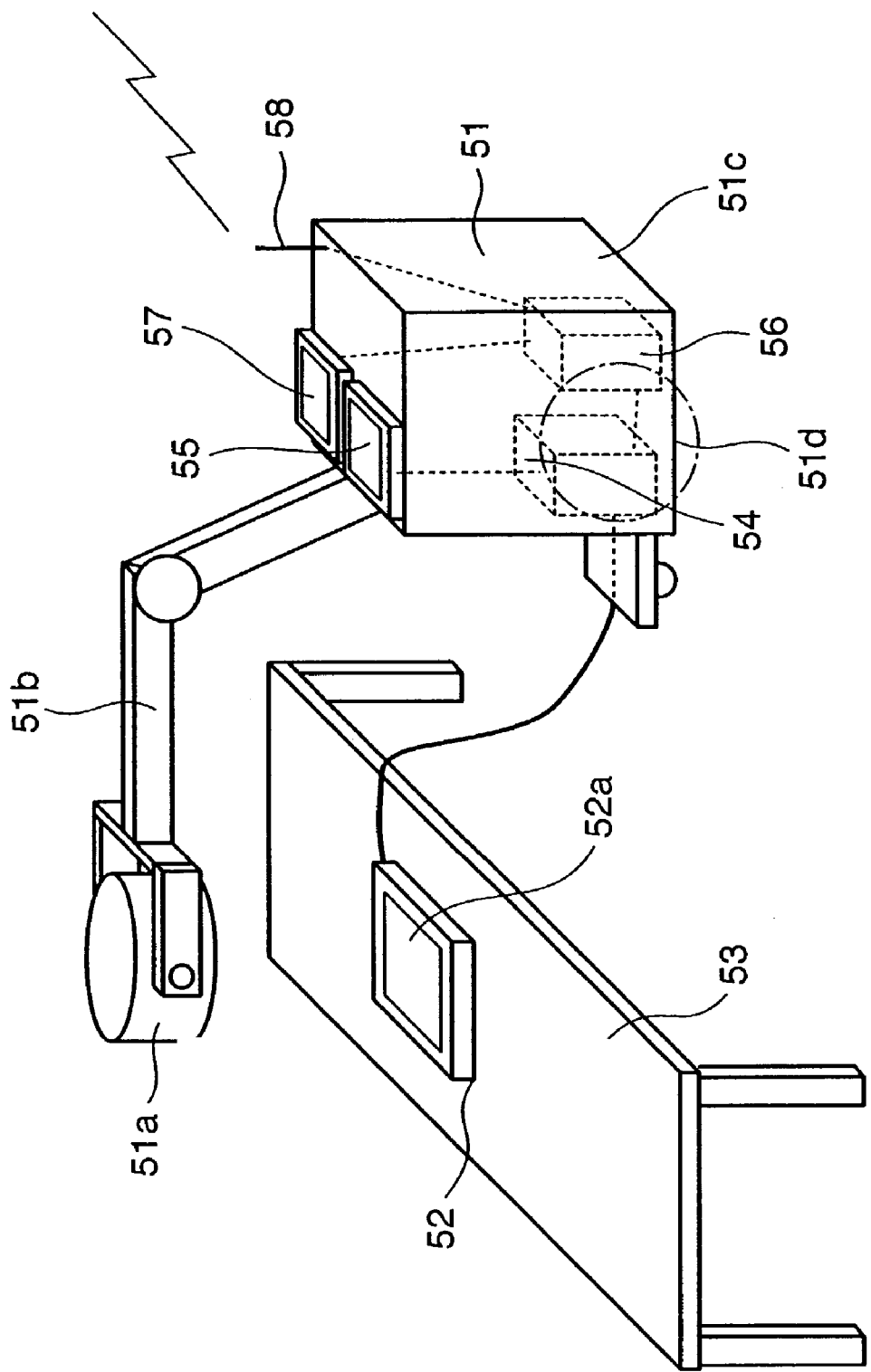
FIG. 2 is a schematic perspective view showing the specific arrangement of the X-ray imaging system according to the first embodiment of the present invention.

FIG. 2 is a schematic perspective view showing the specific arrangement of the X-ray imaging system according to the first embodiment of the present invention.

Reference numeral 51 denotes a mobile X-ray imaging apparatus; 52, an X-ray detector corresponding to the X-ray detection units 24, 26, and 28; 53, a bed; 51a, an X-ray generating unit which emits X-rays; 51b, a movable arm which supports the X-ray generating unit 51a so as to allow it to move in accordance with an imaging direction and imaging position (imaging target region); 51c, a housing which supports the movable arm 51b; and 51d, wheels to be used for movement.

The housing 51c houses a communication device 56 and control unit 54. The communication device 56 incorporates the communication unit 23a and information storage unit 23b. Reference numeral 58 denotes an antenna for communication; and 57, a display device corresponding to the information display unit 23c which displays imaging request information and the like. The control unit 54 controls the operations of the respective components of the mobile X-ray imaging apparatus including the X-ray detector 52 and X-ray generating unit 51a, and incorporates the image storage unit 23d and an image processing unit (not shown).

The control unit 54, for example, sets imaging conditions and/or image processing conditions on the basis of the imaging target region and/or imaging direction contained in imaging request information (controls the X-ray detector, X-ray generating unit and/or image processing unit), associates patient information and/or imaging request information with the image data obtained by imaging, and associates the image data obtained by imaging with the transmission destination or transfer destination of the image data based on the imaging request information and the like.

Reference numeral 55 denotes a display device for sensed images, which corresponds to the image display unit 23e. The X-ray detector 52 incorporates an X-ray detection sensor having a detection surface constituted by a plurality of two-dimensionally arranged photoelectric conversion elements. Reference numeral 52a denotes the effective range of the sensor.

Using the mobile X-ray imaging apparatus shown in FIG. 2 allows the operator (X-ray imaging technician) to receive imaging request information by wireless communication and visually check the information on the display device 57. The operator moves to a patient as an imaging target in accordance with the obtained imaging request information, directs the X-ray detector 52 to the imaging target region of the patient, and causes the X-ray generating unit 51a to emit X-rays.

The X-rays transmitted through the patient are detected by the X-ray detector 52 and processed. The resultant image is then quickly displayed on the image display device 55. This allows the operator to immediately check whether the imaging operation has been properly performed. Using a high-resolution display device makes it possible to make image interpretation and diagnosis at the site of imaging operation.

As described above, according to the first embodiment, there are provided a mobile X-ray imaging apparatus and X-ray imaging system which can improve the working efficiency of the technician by, for example, omitting information input operation and speeding up information communication, reduce the load, and improve reliability of information communication by, for example, eliminating posting errors.

<Second Embodiment>

Figure 3:
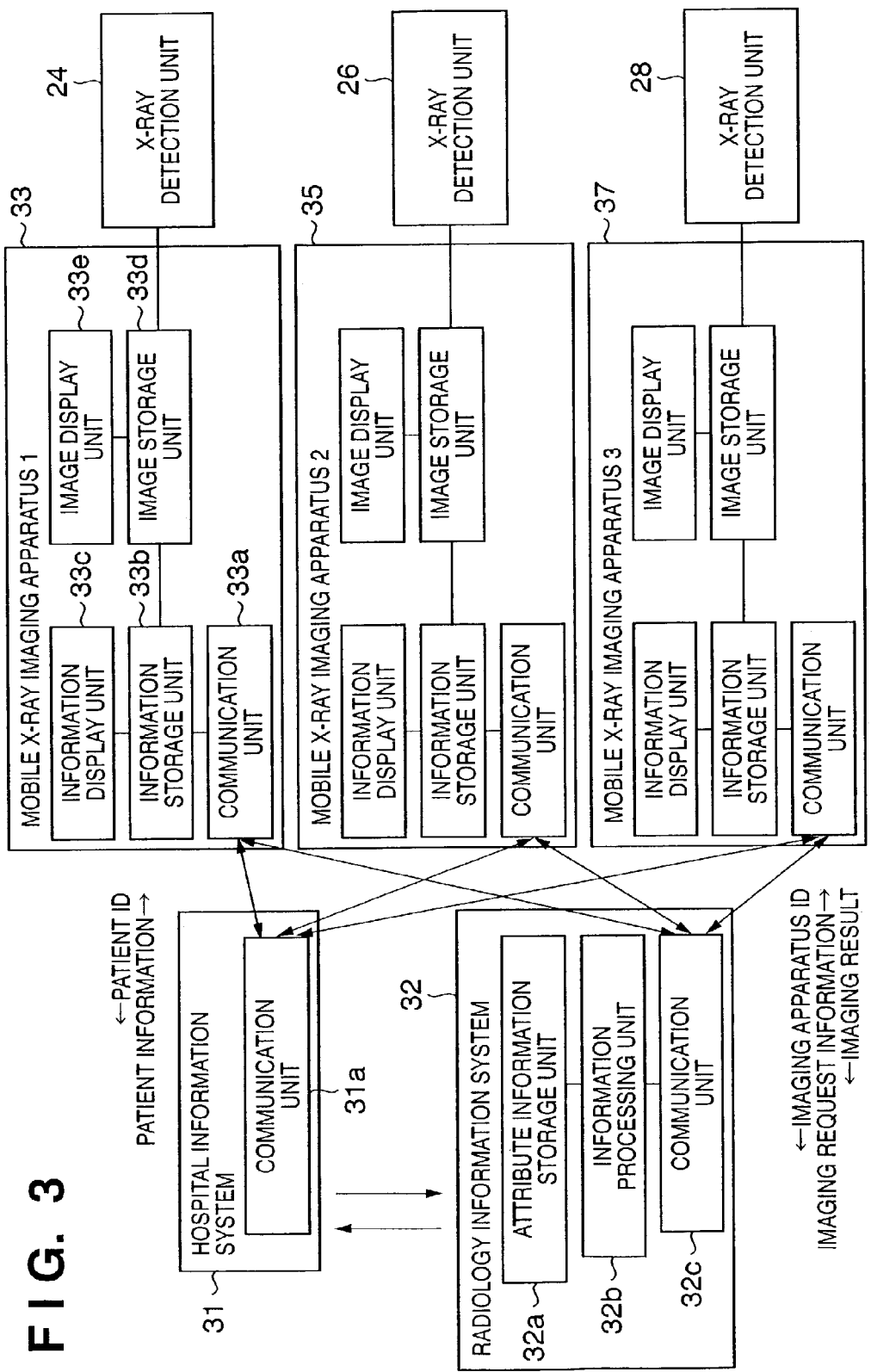
FIG. 3 is a block diagram showing the schematic arrangement of an X-ray imaging system according to the second embodiment of the present invention.

FIG. 3 is a block diagram showing the schematic arrangement of an X-ray imaging system according to the second embodiment of the present invention.

Note that the same reference numerals as in FIG. 1 in the first embodiment denote the same parts in FIG. 3. The second embodiment differs from the first embodiment in that a communication unit 33a of a mobile X-ray imaging apparatus 33 can communicate with a communication unit 31a installed in a hospital information system 31 as well as a communication unit 32c of a radiology information system 32. Units 32a, 32b, 33b, 33c, 33d, and 33e in FIG. 3 respectively have the same functions as those of the units 22a, 22b, 23b, 23c, 23d, and 23e in FIG. 1.

According to the second embodiment having this arrangement, the mobile X-ray imaging apparatus 33 and mobile X-ray imaging apparatuses 35 and 37 each can receive patient information from the hospital information system 31 by transmitting, to the hospital information system 31, the patient ID of a patient as an imaging target contained in the imaging request information received from the radiology information system 32.

With this operation, since information to be communicated can be distributed, the time for one communication can be shortened. That is, the operator starts moving upon receiving only imaging request information within a short period of time, and can receive detailed patient information while moving until imaging operation. This makes it possible to improve the working efficiency.

<Third Embodiment>

Figure 4:
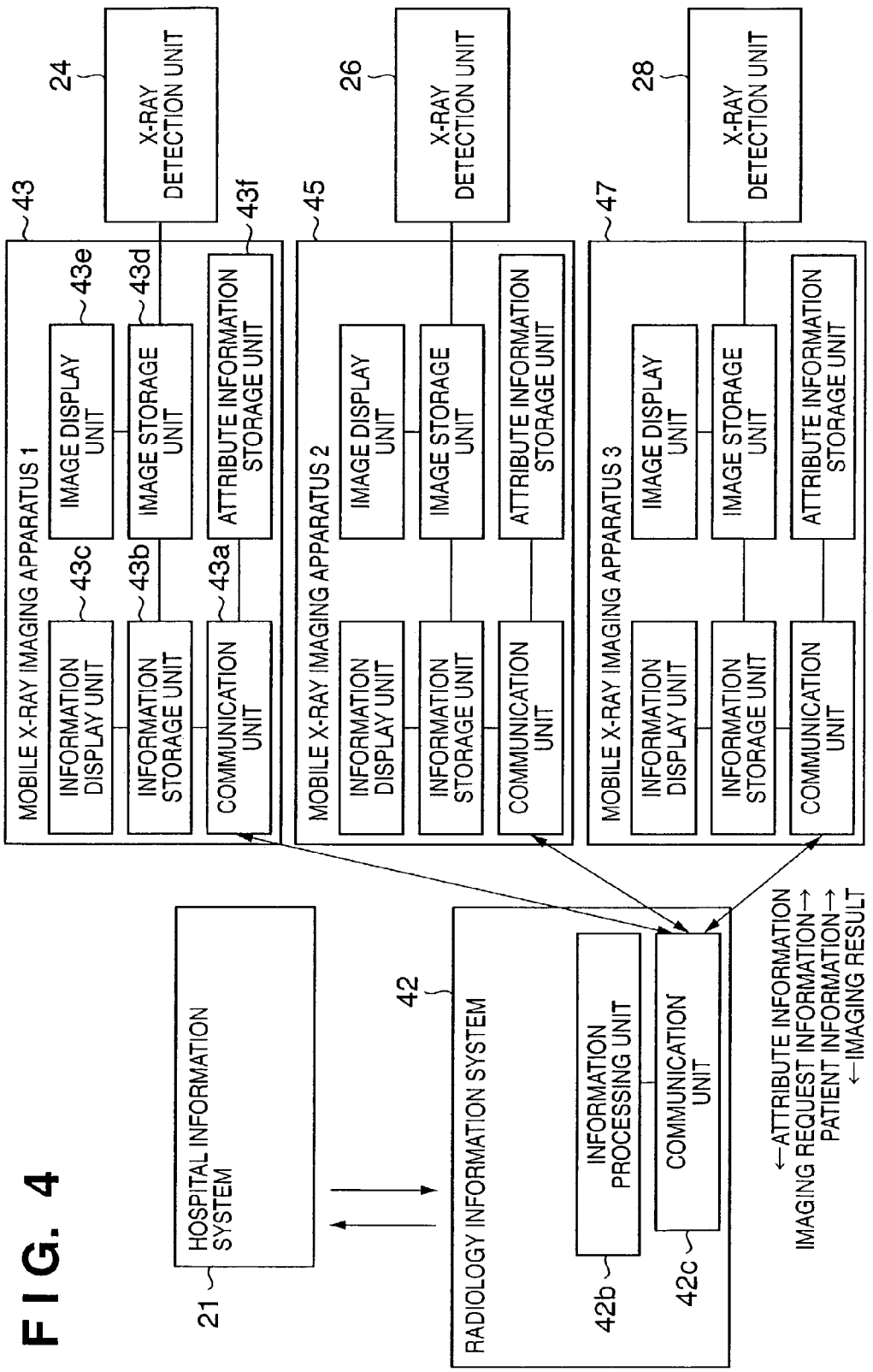
FIG. 4 is a block diagram showing the schematic arrangement of an X-ray imaging system according to the third embodiment of the present invention.

FIG. 4 is a block diagram showing the schematic arrangement of an X-ray imaging system according to the third embodiment of the present invention.

Note that the same reference numerals as in FIG. 1 in the first embodiment denote the same parts in FIG. 4. The third embodiment differs from the second embodiment in that the attribute information storage unit 22a incorporated in the radiology information system 22 is incorporated as an attribute information storage unit 43f in each of mobile X-ray imaging apparatuses 43, 45, and 47. Units 42b, 42c, 43a, 43b, 43c, 43d, and 43e in FIG. 4 respectively have the same functions as those of the units 22b, 22c, 23a, 23b, 23c, 23d, and 23e in FIG. 1.

According to the third embodiment having this arrangement, since the attribute information storage unit 43f is incorporated in each mobile X-ray imaging apparatus, the operator (X-ray imaging technician) can easily change attribute information. This allows the operator to quickly cope with a case wherein, for example, imaging is to be done in a ward different from the usual one.

In this case, the corresponding attribute information itself is transmitted to the radiology information system 22. Upon reception of the attribute information, the radiology information system 22 selects (retrieves) imaging request information based on the received attribute information, and transmits the selected imaging request information to the mobile X-ray imaging apparatus which has transmitted the attribute information.

The imaging apparatus ID in the first embodiment and the attribute information in the third embodiment each function as selection (retrieval) key information to be transmitted from the mobile X-ray imaging apparatus to the radiology information system 22 in order to select (retrieve) target imaging request information from the pieces of imaging request information held by the radiology information system 22.

<Fourth Embodiment>

Figure 5:
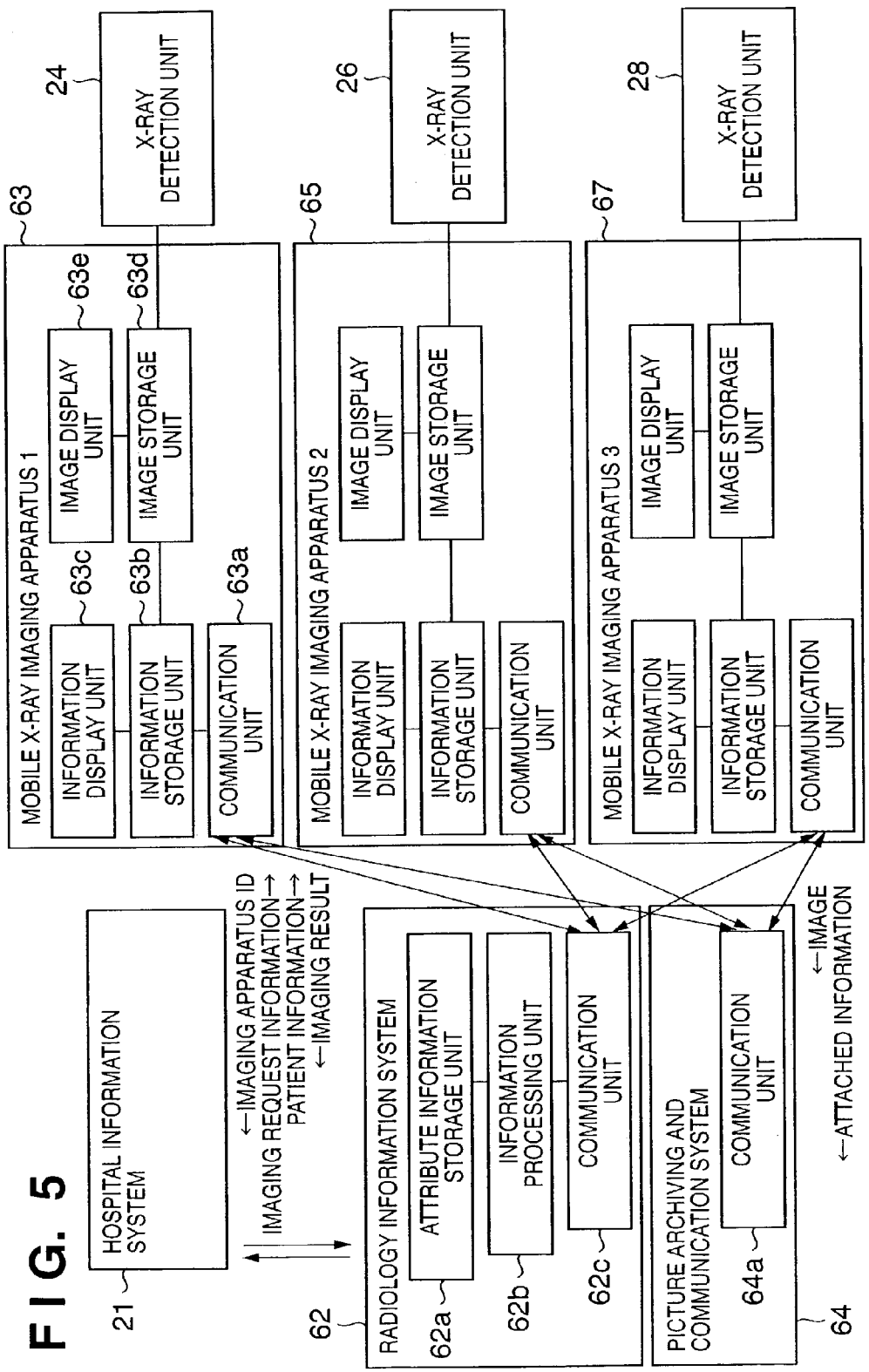
FIG. 5 is a block diagram showing the schematic arrangement of an X-ray imaging system according to the fourth embodiment of the present invention.
Figure 6:
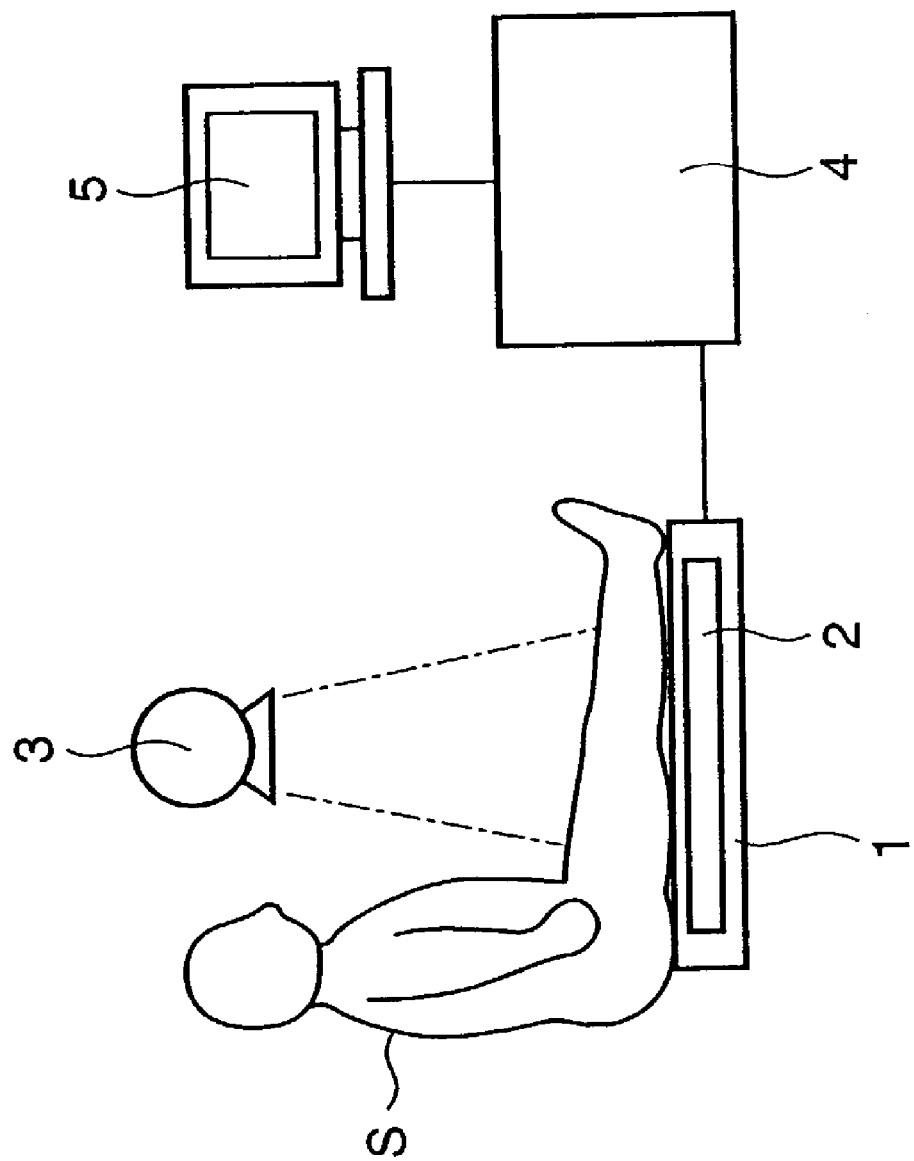
FIG. 6 is a schematic view of a conventional X-ray imaging system.
Figure 7:
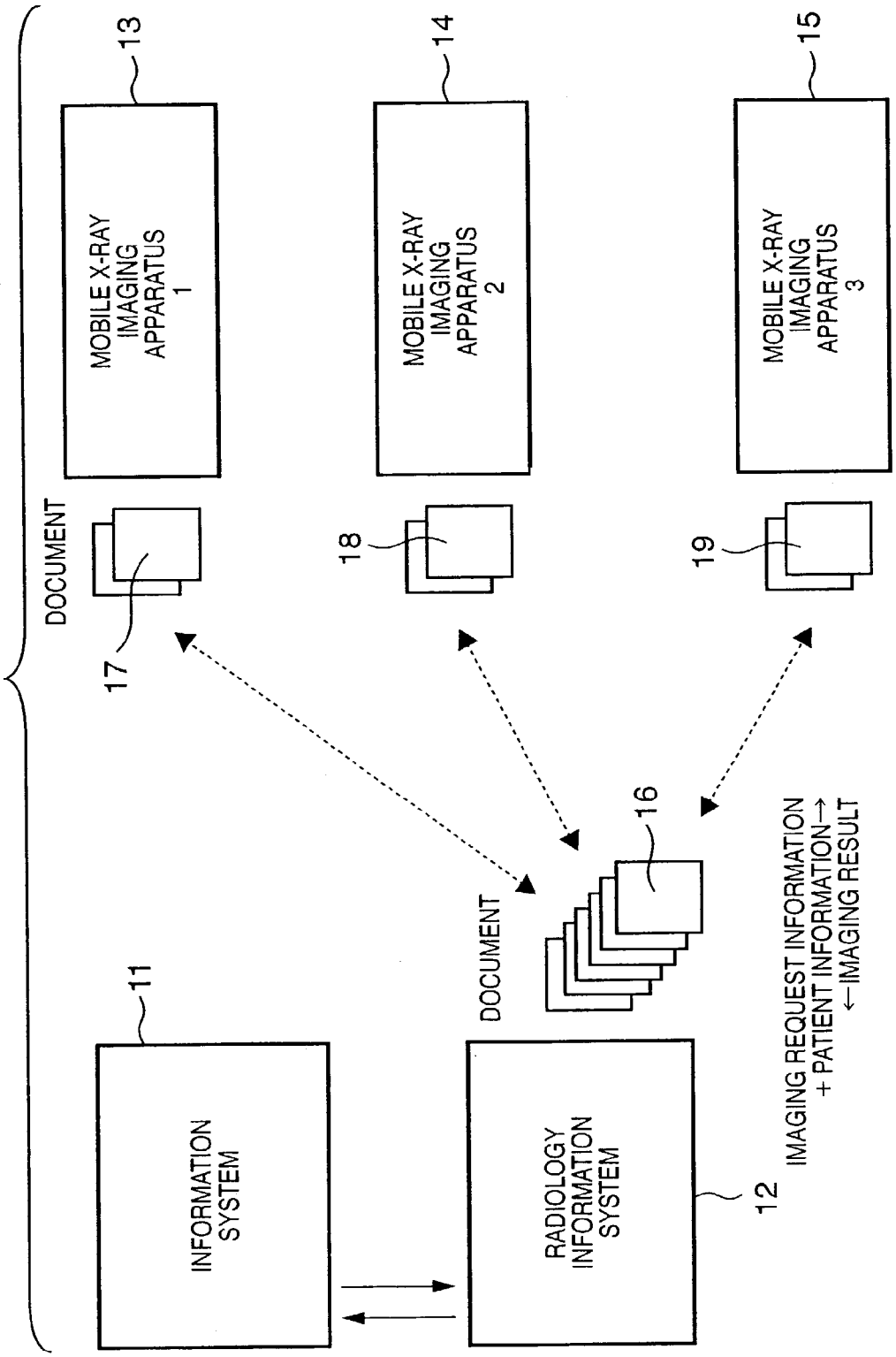
FIG. 7 is a schematic view of a conventional information system in a hospital.

FIG. 5 is a block diagram showing the schematic arrangement of an X-ray imaging system according to the fourth embodiment of the present invention.

Note that the same reference numerals as in FIG. 1 in the first embodiment denote the same parts in FIG. 5. The fourth embodiment differs from the first embodiment in that, for example, a communication unit 63a of a mobile X-ray imaging apparatus 63 can communicate with a communication unit 64a installed in a picture archiving and communication system 64 as well as a communication unit 62c of a radiology information system 62. Units 62a, 62b, 63a, 63b, 63c, 63d, and 63e respectively have the same functions as those of the units 22a, 22b, 23a, 23b, 23c, 23d, and 23e in FIG. 1.

According to the fourth embodiment having this arrangement, for example, the mobile X-ray imaging apparatus 63 can transmit sensed image data to the picture archiving and communication system 64, with patient information and imaging information being attached to the data.

Therefore, immediately after imaging, the resultant image can be displayed in any place inside the hospital through a network in the hospital. For example, immediately after a patient is imaged in a patient's room, a doctor in a separate place can check the sensed image and make a diagnosis of the patient. This makes it possible to realize quick determination and treatment.

In addition, automatically transferring sensed images after imaging operation will prevent failure to archive the sensed images, and hence realize more reliable image management.

<Fifth Embodiment>

Figure 8:
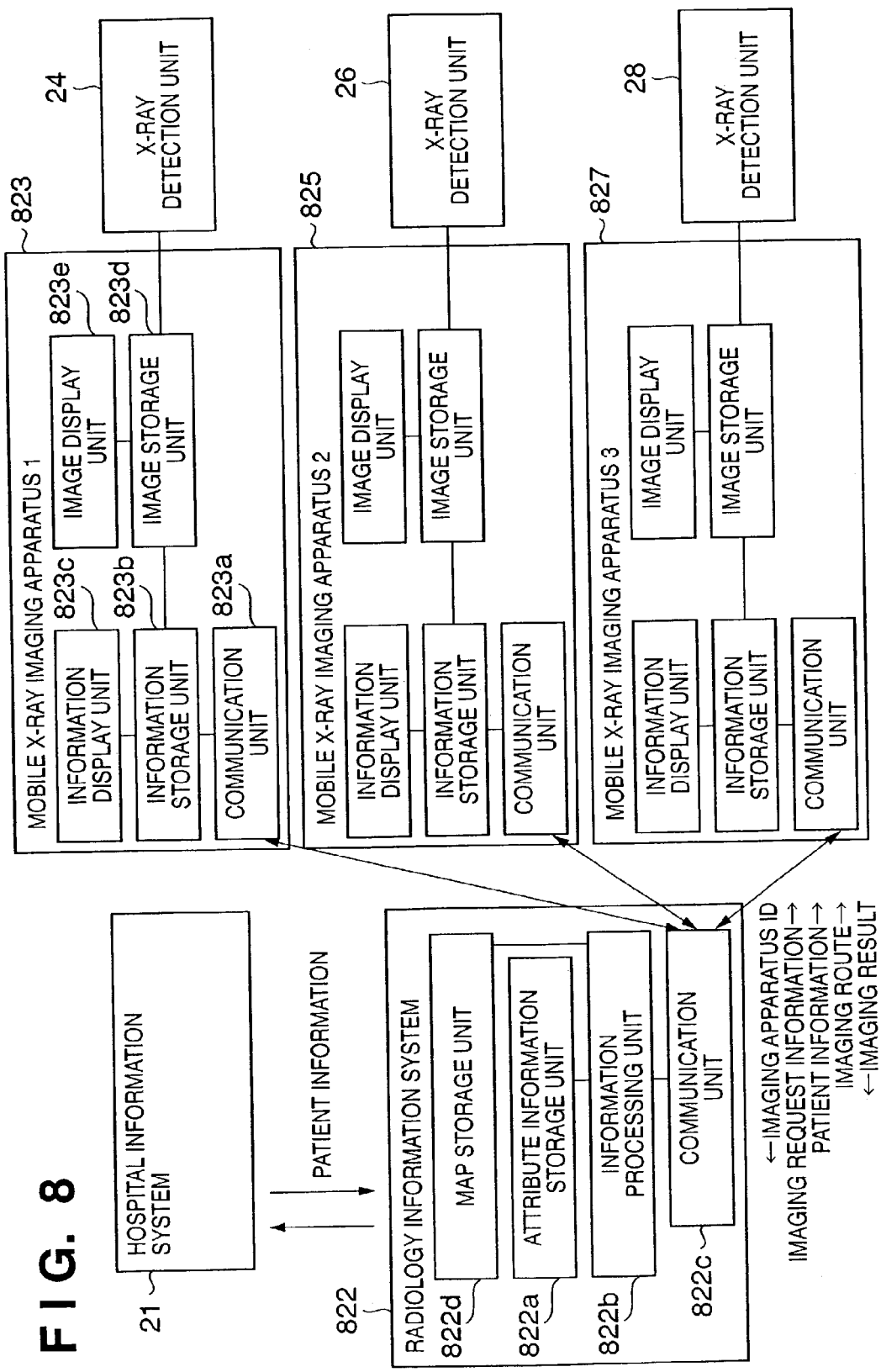
FIG. 8 is a block diagram showing the schematic arrangement of an X-ray imaging system according to the fifth embodiment of the present invention.

FIG. 8 is a block diagram showing the schematic arrangement of an X-ray imaging system according to the fifth embodiment of the present invention.

Referring to FIG. 8, reference numeral 821 denotes a hospital information system; 822, a radiology information system; 823, 825, and 827, first, second, and third mobile X-ray imaging apparatuses;, and 824, 826, and 828, X-ray detection units connected to the mobile X-ray imaging apparatuses 823, 825, and 827. The mobile X-ray imaging apparatuses 823, 825, and 827 have the same arrangement. The following description will be made by using the mobile X-ray imaging apparatus 823 as a representative.

Note that the same reference numerals as in FIG. 1 in the first embodiment denote the same parts in FIG. 8. The fifth embodiment differs from the first embodiment in that the radiology information system 822 has a map storage unit 822d which stores in-hospital map data inside the hospital in which this system is constructed. Units 822a, 822b, 823a, 823b, 823c, 823d, and 823e in FIG. 8 respectively have the same functions as those of the units 22a, 22b, 23a, 23b, 23c, 23d, and 23e in FIG. 1.

Distribution and sorting processing of imaging request information by the radiology information system 822 will be described next with reference to FIG. 9.

Figure 9:
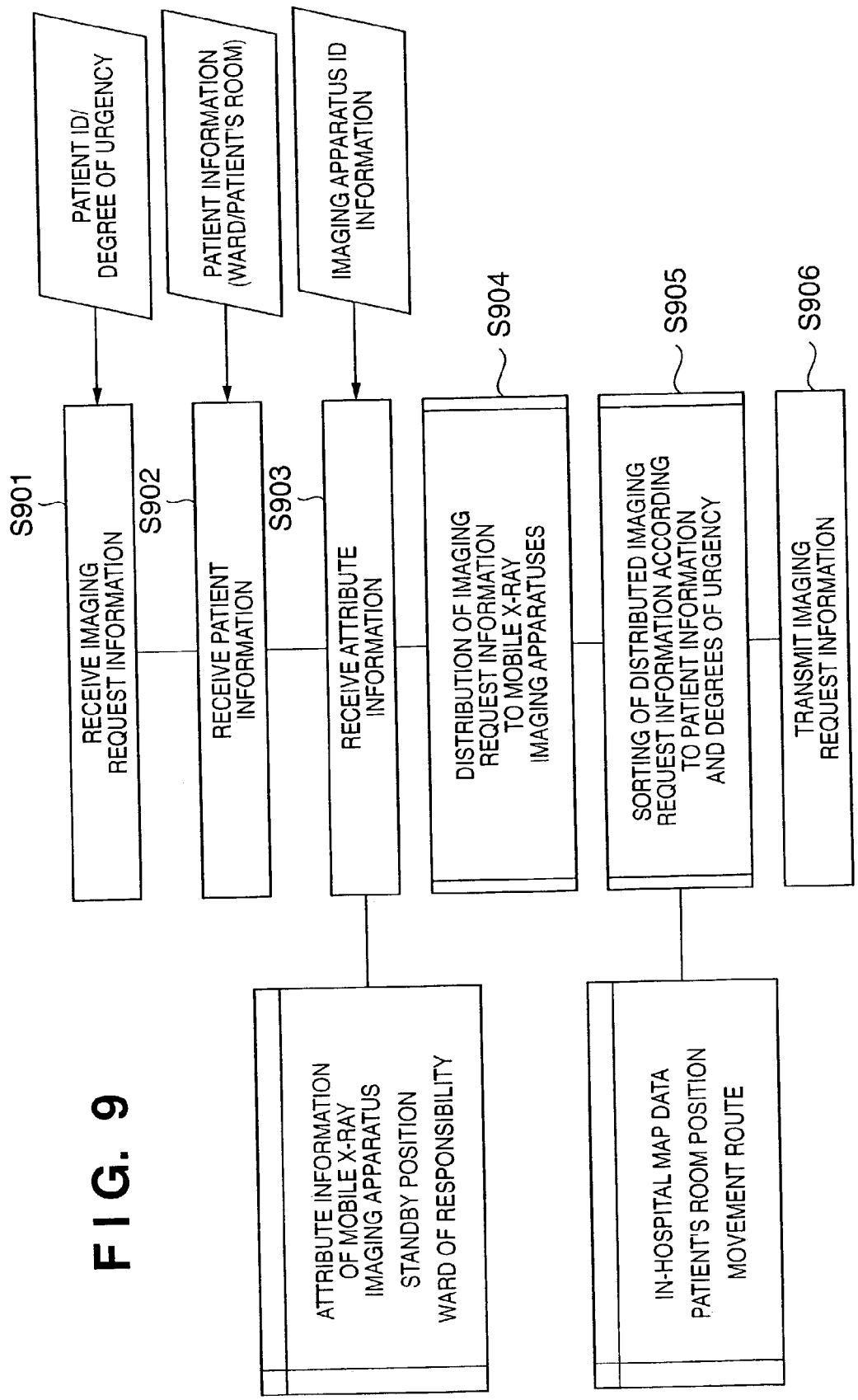
FIG. 9 is a flow chart showing processing executed by the radiology information system according to the fifth embodiment of the present invention.

FIG. 9 is a flow chart showing the processing executed by the radiology information system according to the fifth embodiment of the present invention.

As described above, the hospital information system 821 handles overall in-hospital management information such as patient information (e.g., patient IDs, patient names, patients' wards/room numbers, sexes, and dates of birth) and accounting information. Likewise, the radiology information system 822 manages imaging request information concerning imaging operation, e.g., receiving an imaging request from the diagnosis/treatment department and outputting an imaging request to the radiology department upon clarifying a specific patient, specific region, and specific imaging equipment to be used for imaging operation. The hospital information system 821 and radiology information system 822 are connected to each other through a network inside the hospital to exchange necessary information with each other.

The radiology information system 822 according to the fifth embodiment receives imaging request information from an imaging request system in each diagnosis/treatment department (step S901). Note that the degree of urgency indicating how urgent the request is (e.g., degree of urgency 3: highest priority, degree of urgency 2: ordinary, and degree of urgency 1: arbitrary) is added to this imaging request information.

The information processing unit 822b receives each patient information from the hospital information system 821 on the basis of the patient ID attached to the imaging request information (step S902). Note that the received patient information contains the patient's ward and room number.

The information processing unit 822b then receives the imaging apparatus ID and acquires attribute information associated with the imaging apparatus ID (step S903).

First of all, the information processing unit 822b distributes pieces of imaging request information according to the pieces of attribute information of the respective mobile X-ray imaging apparatuses (step S904). The information processing unit 822b then sorts the respective pieces of imaging request information in imaging order by collating the room numbers of the patients (position information concerning the positions of the objects (patients)) with the in-hospital map data stored in the map storage unit 822d.

More specifically, the information processing unit 822b specifies the positions of the patients from the patients' room numbers, and calculates a shortest movement route from the movement routes stored in the map storage unit 822d together with the in-hospital map data, thereby sorting the respective pieces of imaging request information (step S905).

In addition, the information processing unit 822b can determine a route with higher priorities being given to imaging operations with higher degrees of urgency according to the degrees of urgency of the pieces of imaging request information, even if the determined route is not the shortest route. The pieces of imaging request information for the respective mobile X-ray imaging apparatuses, which have been distributed and sorted, are wirelessly transmitted to the mobile X-ray imaging apparatuses 823, 825, and 827 by the communication unit 822c (step S906).

More specifically, as in the first embodiment, the communication unit 823a transmits the imaging apparatus IDs of the respective mobile X-ray imaging apparatuses to the radiology information system 822. With this operation, in the radiology information system 822, the information processing unit 822b recognizes the imaging apparatuses IDs, and transmits the imaging requests sorted according to the attribute information to the corresponding mobile X-ray imaging apparatuses.

For example, therefore, upon transmitting a desired imaging apparatus ID by operating a switch (not shown) and acquiring imaging request information and patient information, the operator (X-ray imaging technician) of the mobile X-ray imaging apparatus 823 can visually check the imaging request information, patient information, and the imaging order determined by sorting, the imaging route, and the like on the information display unit 823*c*. The operator can execute imaging in accordance with the visually checked contents.

In addition, the operator may acquire the in-hospital map data stored in the map storage unit 822*d* of the radiology information system 822 by using the communication unit 823*a*, and display the in-hospital map data on the information display unit 823*c*. Furthermore, display control may be performed to explicitly indicate the position (room) of the patient to be imaged next and a route to the position on the in-hospital map data at the same time when the in-hospital map data is displayed.

As a specific arrangement for the X-ray imaging system according to the fifth embodiment, for example, an arrangement similar to that shown in FIG. 2 in the first embodiment may be applied.

When the mobile X-ray imaging apparatus 51 shown in FIG. 2 is used, in particular, the operator (X-ray imaging technician) can receive imaging request information, an imaging order, and an imaging route from the radiology information system 822 by wireless communication, and visually check them on the display device 57. The operator sequentially moves to a patient as an imaging target in accordance with the displayed imaging order and imaging route, directs the X-ray detector 52 to the imaging target region of the patient, and irradiates the region with X-rays from the X-ray generating unit 51*a*.

The X-rays transmitted through the patient are detected by the X-ray detector 52 and processed. The resultant image is quickly displayed on the image display device 55. This allows the operator to follow the most efficient imaging route and perform efficient work. In addition, the operator can immediately determine whether imaging has been properly done. Using a high-resolution display device makes it possible to make image interpretation and diagnosis at the site of imaging operation.

<Sixth Embodiment>

Figure 10:
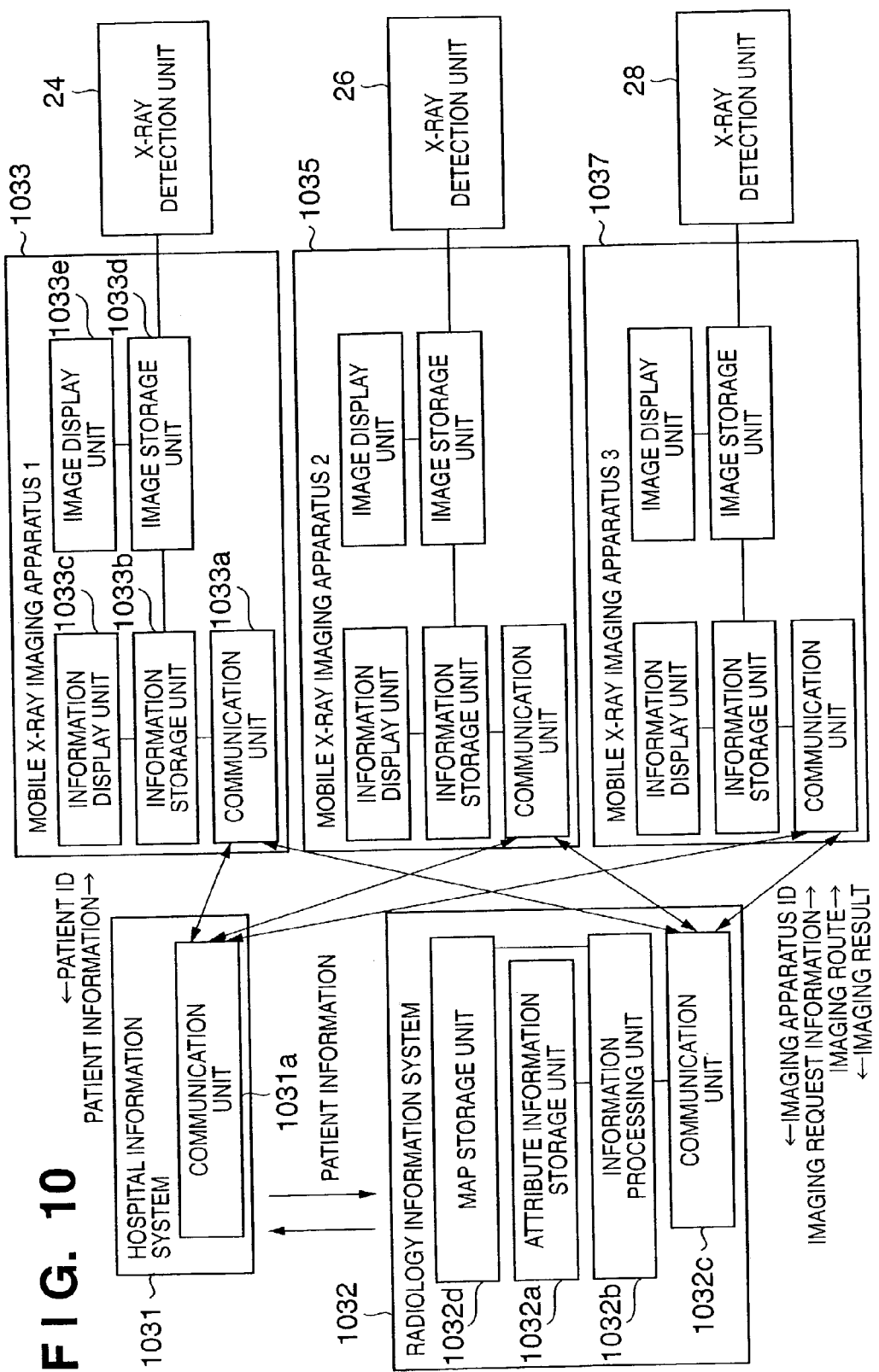
FIG. 10 is a block diagram showing the schematic arrangement of an X-ray imaging system according to the sixth embodiment of the present invention.

FIG. 10 is a block diagram showing the schematic arrangement of an X-ray imaging system according to the sixth embodiment of the present invention.

The same reference numerals as in FIG. 8 in the fifth embodiment denote the same parts in FIG. 10. The sixth embodiment differs from the fifth embodiment in that a communication unit 1033*a* of a mobile X-ray imaging apparatus 1033 can communicate with a communication unit 1031*a* installed in a hospital information system 1031 as well as a communication unit 1032*c* of a radiology information system 1032. Units 1032*a*, 1032*b*, 1032*d*, 1033*b*, 1033*c*, 1033*d*, and 1033*e* in FIG. 10 respectively have the same functions as those of the units 822*a*, 822*b*, 822*d*, 823*b*, 823*c*, 823*d*, and 823*e* in FIG. 8.

According to the sixth embodiment having this arrangement, in addition to the effect described in the fifth embodiment, the mobile X-ray imaging apparatus 1033 and mobile X-ray imaging apparatuses 1035 and 1037 can directly receive patient information from the hospital information system 1031 by transmitting, to the hospital information system 1031, the patient IDs of target patients contained in imaging request information received from the radiology information system 1032.

With this operation, since information to be communicated can be distributed (divided), the time for one communication can be shortened. That is, the operator starts moving upon receiving only imaging request information within a short period of time, and can receive detailed patient information while moving until imaging operation. This makes it possible to improve the working efficiency.

<Seventh Embodiment>

Figure 11:
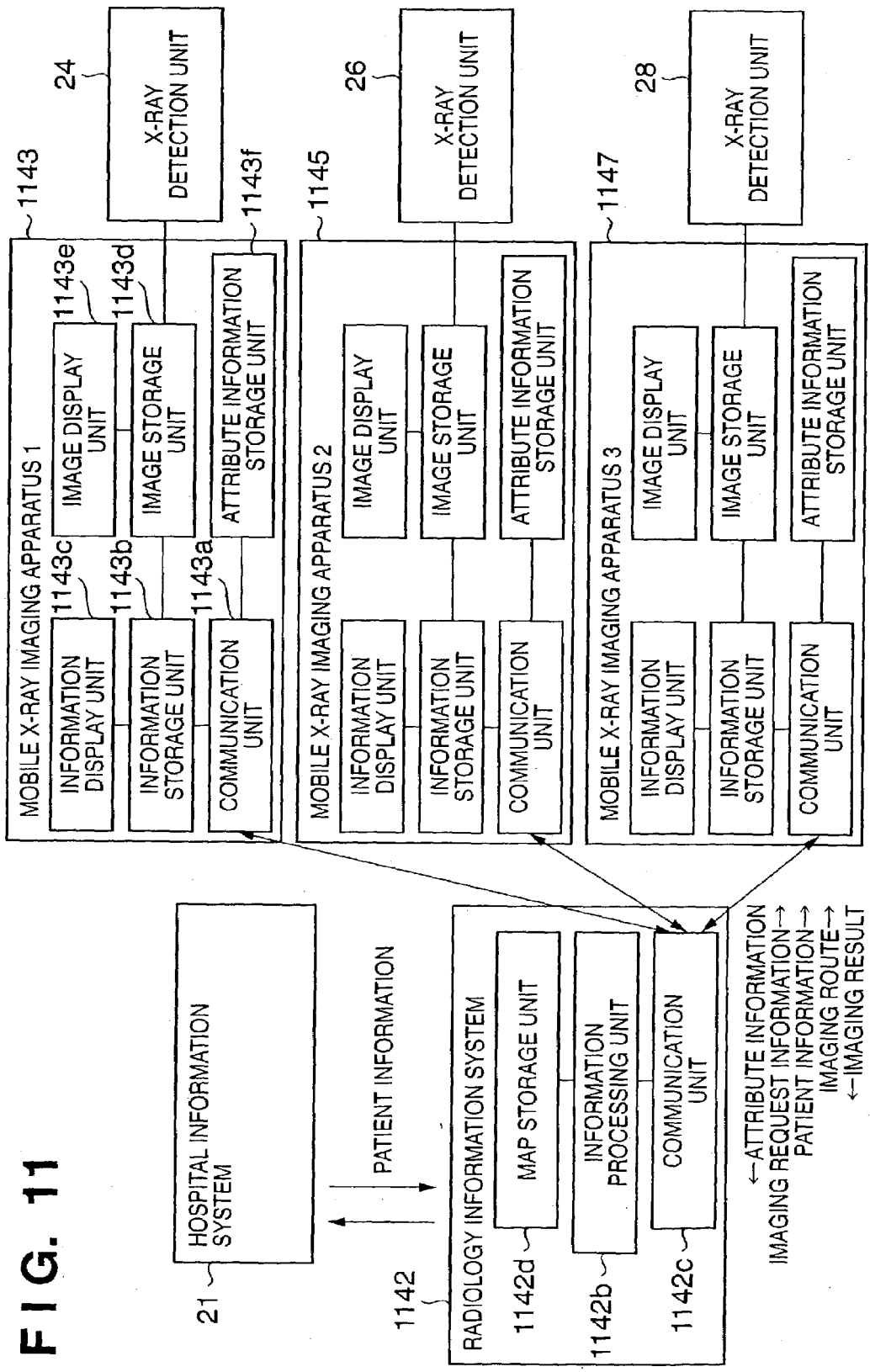
FIG. 11 is a block diagram showing the schematic arrangement of an X-ray imaging system according to the seventh embodiment of the present invention.

FIG. 11 is a block diagram showing the schematic arrangement of an X-ray imaging system according to the seventh embodiment of the present invention.

Note that the same reference numerals as in FIG. 8 in the fifth embodiment denote the same parts in FIG. 11. The seventh embodiment differs from the fifth embodiment in that the attribute information storage unit 822*a* incorporated in the radiology information system 822 is incorporated as an attribute information storage unit 1143*f* in each of mobile X-ray imaging apparatuses 1143, 1145, and 1147. Units 1142*b*, 1142*c*, 1143*a*, 1143*b*, 1143*c*, 1143*d*, and 1143*e* in FIG. 11 respectively have the same functions as those of the 822*b*, 822*c*, 823*a*, 823*b*, 823*c*, 823*d*, and 823*e*.

According to the seventh embodiment having this arrangement, in addition to the effect described in the fifth embodiment, since the attribute information storage unit 1143*f* is incorporated in each of the mobile X-ray imaging apparatuses, the operator (X-ray imaging technician) can easily change attribute information. This allows the operator to quickly cope with a case wherein, for example, imaging is to be done in a ward different from the usual one.

<Eighth Embodiment>

Figure 12:
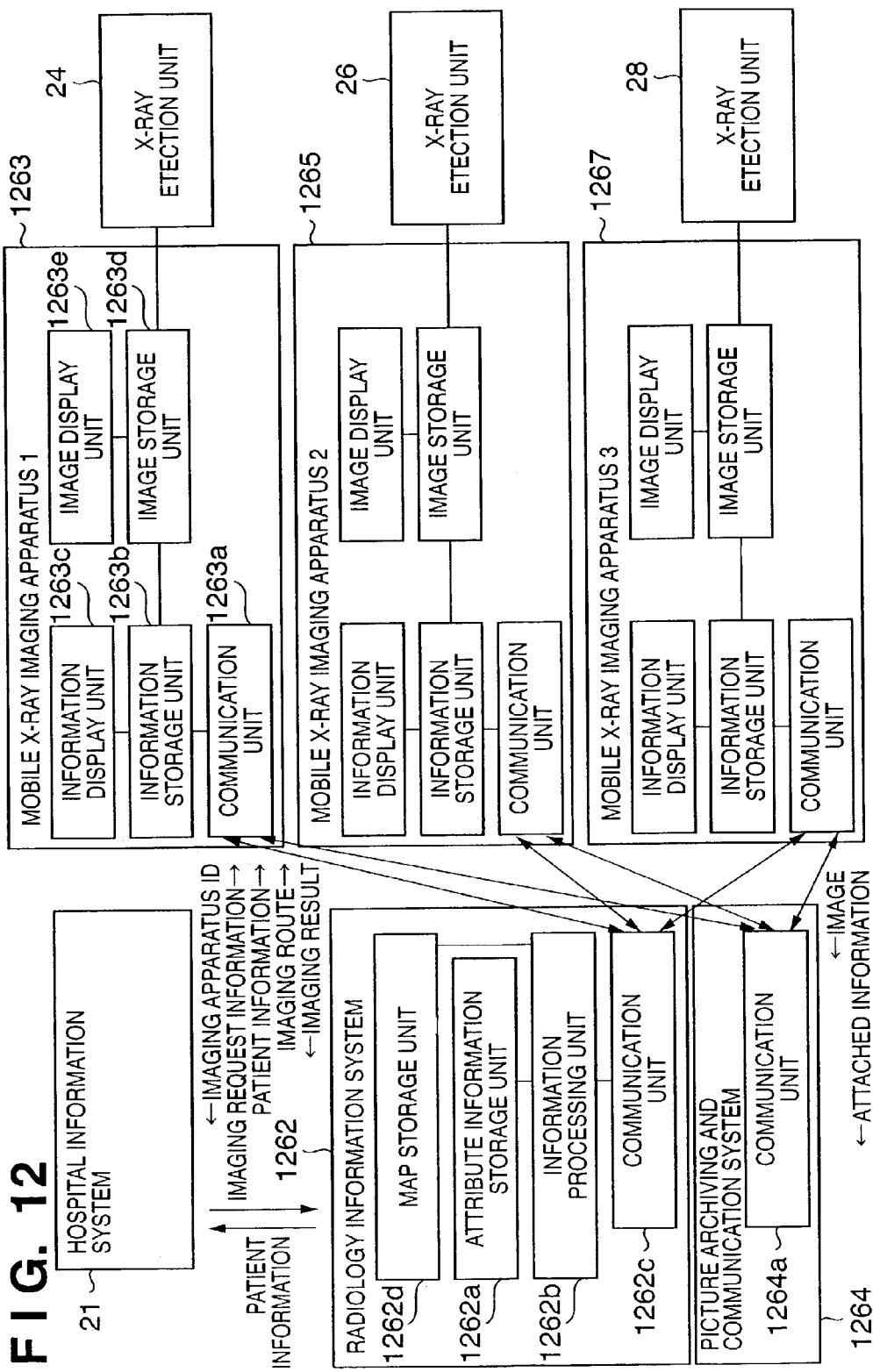
FIG. 12 is block diagram showing the schematic arrangement of an X-ray imaging system according to the eighth embodiment of the present invention.

FIG. 12 is a block diagram showing the schematic arrangement of an X-ray imaging system according to the eighth embodiment of the present invention.

Note that the same reference numerals as in FIG. 8 in the fifth embodiment denote the same parts in FIG. 12. The eighth embodiment differs from the fifth embodiment in that a communication unit 1263*a* of a mobile X-ray imaging apparatus 1263 can communicate with a communication unit 1264*a* installed in a picture archiving and communication system 1264 as well as a communication unit 1262*c* of a radiology information system 1262. Units 1262*a*, 1262*b*, 1262*d*, 1263*b*, 1263*c*, 1263*d*, and 1263*e* in FIG. 12 respectively have the same functions as those of the units 822*a*, 822*b*, 822*d*, 823*b*, 823*c*, 823*d*, and 823*e*.

According to the eighth embodiment having this arrangement, in addition to the effect described in the fifth embodiment, for example, the mobile X-ray imaging apparatus 1263 can transmit sensed image data to the picture archiving and communication system 1264 upon attaching patient information, imaging information, and the like to the data.

Therefore, immediately after imaging, the resultant image can be displayed in any place inside the hospital through a network in the hospital. For example, immediately after a patient is imaged in a patient's room, a doctor in a separate place can check sensed image and make a diagnosis of the patient. This makes it possible to realize quick determination and treatment.

In addition, automatically transferring sensed images after imaging operation will prevent failure to archive the sensed images, and hence realize more reliable image management.

The embodiments of the present invention are not limited to the above embodiments described above, and various modifications to the embodiments are conceivable.

For example, each of the fifth to eighth embodiments has exemplified the case wherein the information processing unit for computing an imaging route is mounted in the radiology information system. A function similar to this function may be implemented in another place. For example, this function may be implemented in a mobile X-ray imaging apparatus (a controller for an X-ray detector or the like). Alternatively, an information processing unit may be mounted in one of a plurality of mobile X-ray imaging apparatuses, and processed image interpretation may be communicated to the remaining apparatuses.

Imaging request information may be communicated to a portable information terminal that can be carried by an imaging technician to be displayed on the terminal. In this case, the imaging technician visually checks the imaging request information through this portable information terminal and performs imaging on the basis of the check result.

Imaging request information may be input to a mobile X-ray imaging apparatus as the need arises instead of being collectively input to the apparatus at the start of imaging. For example, an urgent additional imaging request may be input to the apparatus in the process of imaging or a change request may be input for imaging operation that has been requested. In this case, information indicating the progress of imaging in the imaging order may be input to the radiology information system by using some means, and the radiology information system computes an optimal route again inconsideration of the additional imaging request or change request, thus transmitting the resultant imaging request information to the mobile X-ray imaging apparatus.

In determining one of a plurality of mobile X-ray imaging apparatuses to which the added imaging request information should be transmitted, the approximate positions of the respective mobile X-ray imaging apparatuses may be estimated from the elapsed time of the occurrence time of the first imaging request information, and an apparatus that can process the added imaging request information most efficiently may be estimated.

By adding a system which detects the positions of mobile X-ray imaging apparatuses in real time by using, for example, GPS, more efficient operation can be realized. For example, in-hospital map data is displayed on the information display unit of a mobile X-ray imaging apparatus, and the current position of the apparatus can be displayed on the in-hospital map data. In addition, a route for the next destination can be displayed on the in-hospital map data. Furthermore, the imaging technician may be guided to the destination by voice.

At the occurrence of an urgent imaging request, the request can be quickly handled by transmitting the imaging request information to a mobile X-ray imaging apparatus located closest to the current position of the target patient. Such imaging request management can also be realized by using a display apparatus, in the centralized management room in the hospital, which displays in-hospital map data and the current positions of the respective mobile X-ray imaging apparatuses in real time.

As described above, each of the X-ray imaging apparatuses according to the fifth to eighth embodiments can achieve an improvement in the efficiency of imaging operation, quick handling of an urgent request, a reduction in load on an operator, and the like by making the information processing unit perform distribution of imaging requests and determination of an imaging order which have been manually performed in the prior art.

<Other Embodiment>

The embodiments of the present invention are not limited to those described above, and can be variously modified. When wireless communication is to be used as an information communication means, TCP/IP, Bluetooth, or the like which is used for a general wireless LAN can be used as a wireless communication protocol.

Wireless communication may be done in any place in the hospital in accordance with the infrastructure of the hospital or may be limited to a place where wireless communication can be done. In addition, wire communication may be done. In this case, a wire communication system using a detachable communication cable may be used. Alternatively, information may be communicated by a so-called offline scheme through a portable storage medium such as a floppy (registered trademark) disk, magnetooptical disk, or optical disk. In this case, each mobile X-ray imaging apparatus is configured to incorporate a reading unit for reading a portable storage medium.

In addition, sensed image data may be transmitted from the picture archiving and communication system to a mobile X-ray imaging apparatus, as in case wherein the past images of the corresponding patient are to be referred to, as well as being transmitted from the mobile X-ray imaging apparatus to the picture archiving and communication system.

The functions of the above embodiments can also be realized by directly or remotely supplying software program codes to a system or apparatus and causing the computer of the system or apparatus to read out and execute the program codes.

The program codes themselves which are installed in the computer to allow the computer to implement or execute the function or processing of the present invention also realize the present invention. That is, the computer program itself, which implements the function or processing of the present invention, is also incorporated in the present invention.

In this case, the program may take any form, e.g., an object code, a program executed by an interpreter, and script data supplied to an OS.

As a recording medium for supplying the program, a floppy (registered trademark) disk, hard disk, optical disk, magnetooptical disk (MO), CD-ROM, CD-R, CD-RW, magnetic tape, nonvolatile memory card, ROM, DVD (DVD-ROM or DVD-R), or the like can be used.

This program can also be supplied to the computer by connecting from the computer to a homepage on the Internet by using a browser and downloading the computer program itself or a file containing the compressed program and an automatic install function from the homepage into a storage medium such as a hard disk. Alternatively, the program can be supplied to the computer by downloading the program codes which constitute the program and are divided into a plurality of files from different homepages. That is, a WWW server which provides a user with a program file for causing the computer to realize or execute the function or processing of the present invention is also incorporated as an embodiment in the present invention.

In addition, the following operation is incorporated as an embodiment in the present invention. This program is encrypted and stored in a storage medium such as a CD-ROM. Such storage media are then distributed to users. A user who satisfies a predetermined condition is allowed to download key information for decryption from a homepage through the Internet. The user executes the encrypted program by using the key information to make the computer install the program.

The functions of the above embodiments are realized not only when the readout program is executed by the computer but also when the OS or the like running on the computer performs part or all of actual processing on the basis of the instructions of the program. In such a case, the program is also an embodiment of the present invention.

The functions of the above embodiments are also realized when the program read out from the recording medium is written in the memory of a function expansion board inserted into the computer or a function expansion unit connected to the computer, and the CPU of the function expansion board or function expansion unit or the like performs part or all of actual processing on the basis of the instructions of the program. In such as case, the program is an embodiment of the present invention.

Although the above embodiments have exemplified the X-ray imaging apparatuses, a radiographic of an object can also be acquired by using radiations other than X-rays. Therefore, the X-ray imaging apparatuses can be generalized as radiographic apparatuses.

As many apparently widely different embodiments of the present invention can be made without departing from the spirit and scope thereof, it is to be understood that the invention is not limited to the specific embodiments thereof except as defined in the appended claims.

What is claimed is:

1. A radiographic system comprising:
    a plurality of radiographic apparatuses, each of which is arranged at different positions in radiography;
    an information system having a plurality of radiographic request information;
    a first selection unit arranged to select attribute information corresponding to one of the plurality of radiographic apparatuses;
    a second selection unit arranged to select part of radiographic request information from the plurality of radiographic request information on the basis of the selected attribute information; and
    a transmission unit arranged to transmit the selected radiographic request information to a radiographic apparatus corresponding to the selected attribute information,
    wherein said radiographic apparatus, which corresponds to the selected attribute information, images an object on the basis of the selected radiographic request information, and wherein the attribute information is information concerning a specific range of patients inside a hospital for which each of the plurality of radiographic apparatuses is to perform imaging operation, and the attribute information includes a standby place, the name of a target diagnosis/treatment department, and a name of a technician in charge.

2. The system according to claim 1, wherein the radiographic request information contains information specifying the object.

3. The system according to claim 1, wherein the attribute information contains information associated with the radiographic request information.

4. The system according to claim 1, further comprising an imaging result information transmission unit arranged to transmit imaging result information to the information system.

5. The system according to claim 1, further comprising display unit arranged to display the radiographic request information transmitted by said transmission unit.

6. The system according to claim 1, wherein the information system includes at least one of a hospital information system, a radiology information system, and a picture archiving and communication system.

7. The system according to claim 1, wherein said radiographic apparatus performs at least one of imaging condition setting, image processing condition setting, setting of a transmission destination of the radiographic image data, and association between the radiographic request information and the radiographic image data based on the radiographic request information.

8. The system according claim 1, further comprising sort unit arranged to sort the radiographic request information based on position information concerning a position of the object and map information.

9. The system according to claim 8, further comprising display unit arranged to display the position information concerning the position of the object and the map information.

10. The system according to claim 1, wherein the radiographic apparatus comprises an X-ray detection unit having a plurality of photoelectric conversion elements.

11. An information system comprising:
    a storage unit arranged to store radiographic request information;
    a reception unit arranged to receive key information for selecting the radiographic request information transmitted from a mobile radiographic apparatus which includes a photoelectric conversion element and generates radiographic image data of an object;
    a selection unit arranged to select the radiographic request information stored in said storage unit, based on the key information received by said reception unit;
    a transmission unit arranged to transmit the radiographic request information selected by said selection unit to the mobile radiographic apparatus; and
    sort unit arranged to sort the radiographic request information selected by said selection unit based on position information concerning a position of the object and map information.

* * * * *